United States Patent
Darboux et al.

(10) Patent No.: US 6,594,338 B2
(45) Date of Patent: Jul. 15, 2003

(54) METHOD FOR ESTIMATING SCATTERED RADIATION, IN PARTICULAR FOR CORRECTING RADIOGRAPHY MEASUREMENTS

(75) Inventors: Michel Darboux, Grenoble (FR); Jean-Marc Dinten, Lyons (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/075,968

(22) Filed: Feb. 14, 2002

(65) Prior Publication Data

US 2002/0141541 A1 Oct. 3, 2002

(30) Foreign Application Priority Data

Feb. 16, 2001 (FR) .............................. 01 02139

(51) Int. Cl.[7] .......................... A61B 6/00; G01N 23/083
(52) U.S. Cl. ......................................... 378/98.4; 378/7
(58) Field of Search ..................... 378/7, 62, 98.4

(56) References Cited

U.S. PATENT DOCUMENTS

| | | | |
|---|---|---|---|
| 4,549,307 A | 10/1985 | Macovski | 378/149 |
| 5,615,279 A | 3/1997 | Yoshioka et al. | 382/131 |
| 5,666,381 A | 9/1997 | Ohnesorge et al. | 378/7 |
| 5,774,521 A | * 6/1998 | Close et al. | 378/62 |
| 6,000,847 A | * 12/1999 | Close et al. | 378/207 |
| 2002/0048339 A1 | * 4/2002 | Schneider et al. | 378/7 |

* cited by examiner

*Primary Examiner*—David V. Bruce
(74) *Attorney, Agent, or Firm*—Pearne & Gordon LLP

(57) ABSTRACT

The radiography of a subject is improved by estimating the scattered radiation it transmits to the detectors. For this, one uses scattered radiation measured effectively through a simulacrum of the subject, with analogous attenuation properties, and which are modified by weighted coefficients obtained through a transformation of the values of total radiation received through the subject (3) and the simulacrum (8) selected. Thus it is also possible to improve radiographs without double irradiation of the subject to measure the scattered radiation separately.

10 Claims, 2 Drawing Sheets

Figure 1:
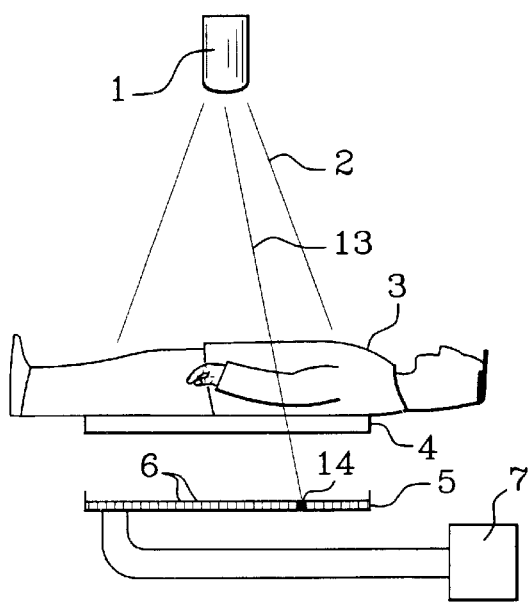

METHOD FOR ESTIMATING SCATTERED RADIATION, IN PARTICULAR FOR CORRECTING RADIOGRAPHY MEASUREMENTS

The present invention relates to a method for estimating scattered radiation, whose main application is intended for the correction of radiographs.

The utilisation of a beam of rays associated with a two-dimensional sensor, very frequently found in radiography, has the disadvantage of producing significant scattered radiation on the radiograph through the subject under examination. In other terms, each of the detectors located behind the subject receives not only a primary radiation, arriving directly from the source in a straight line and having crossed through a well-defined region of the subject, but also scattered radiation of indeterminate origin which disturbs the measurement and which it is therefore desirable to correct.

Several methods are already in use. Thus, the primary radiation can be measured alone if there is strict collimation of the detectors and the source in order to intercept the scattered radiation, but this method, in practice, needs a sweeping of the beam which is slow to carry out, and during which the movements of the patient must be taken into account if one is examining living beings.

The opposite idea has also been suggested, measuring only the scattered radiation. For this, one uses a discontinuous network of absorbers, such as lead balls, between the object and the detectors, to stop the primary radiation locally, such that the detectors located behind these absorbers only measure the scattered radiation. This method, called "beam stop" thus provides two-dimensional tables or maps for the value of the scattered radiation, which are completed by interpolation between the detectors placed behind the absorbers. The diffused radiation thus estimated is subtracted from the total radiation measured separately. This method is precise but has the disadvantage of imposing two irradiations of the subject and thus doubling the dose of radiation it receives. A final example of a method for correcting scattered radiation by material means includes the use of anti-scatter grids, but their efficiency is only partial; it is insufficient for a conical beam, where the scattered radiation can be several times higher than the primary radiation.

Finally, there are a certain number of digital methods for estimating the scattered radiation, for example from convolutions or de-convolutions of measurements; one can also mention the French patent 2 759 800 as an analytic, different digital method. In general, they are complicated to use because they depend on the parameters chosen by the operator (convolution cores, for example) which only provide good results under favourable circumstances, such as small zones where the scattered radiation is low, or objects with relatively homogeneous content. No simple method exists making it possible, for example, to correct the scattered radiation through the thorax or other large anatomical zones, which are frequently examined but which are difficult for correcting the scattered radiation because of their volume and the heterogeneity due to the presence of a complex bone structure whose radiation attenuation capacity is very different from that of soft tissues.

Finally one should mention the U.S. Pat. No. 6,018,565 for the description of a mixed method, with "beam stop" and convolution.

An essential aim of the present invention is to propose a method for estimation and correction for scattered radiation which can suit difficult radiography situations.

The method according to the invention is, in its most general form, a method for estimating scattered radiation coming from an initial radiation having crossed an object and undergone an attenuation allowing a total measurement radiation to pass, characterised by:

drawing up a table of measurements of scattered radiation, obtained by making the initial radiation pass through a simulacrum of the subject, calculation of transposition coefficients between the simulacrum and the subject, according to the initial radiation, the total measurement radiation through the subject and a total measurement radiation through the simulacrum, and a weighting of the measurement table with the transposition coefficients.

Advantageously, the simulacrum will be a block of constant thickness and of a homogeneous material, having an attenuation similar to a base material of the subject; in general the measurement table will be drawn up from a selection in a series of measuring tables for scattered radiation, obtained beforehand by passing the initial radiation successively through a respective series of simulacra of the subject, of different but constant thicknesses; the selection will be made by comparison of a total measurement radiation value through the subject and a total measurement radiation value through the simulacra.

The weighting coefficients are generally value ratios of a same functional calculated for the subject and for the simulacrum. The functional used can be equal to the product of the total measurement radiation by the logarithm of the ratio of total measurement radiation and the initial radiation.

Figure 2:
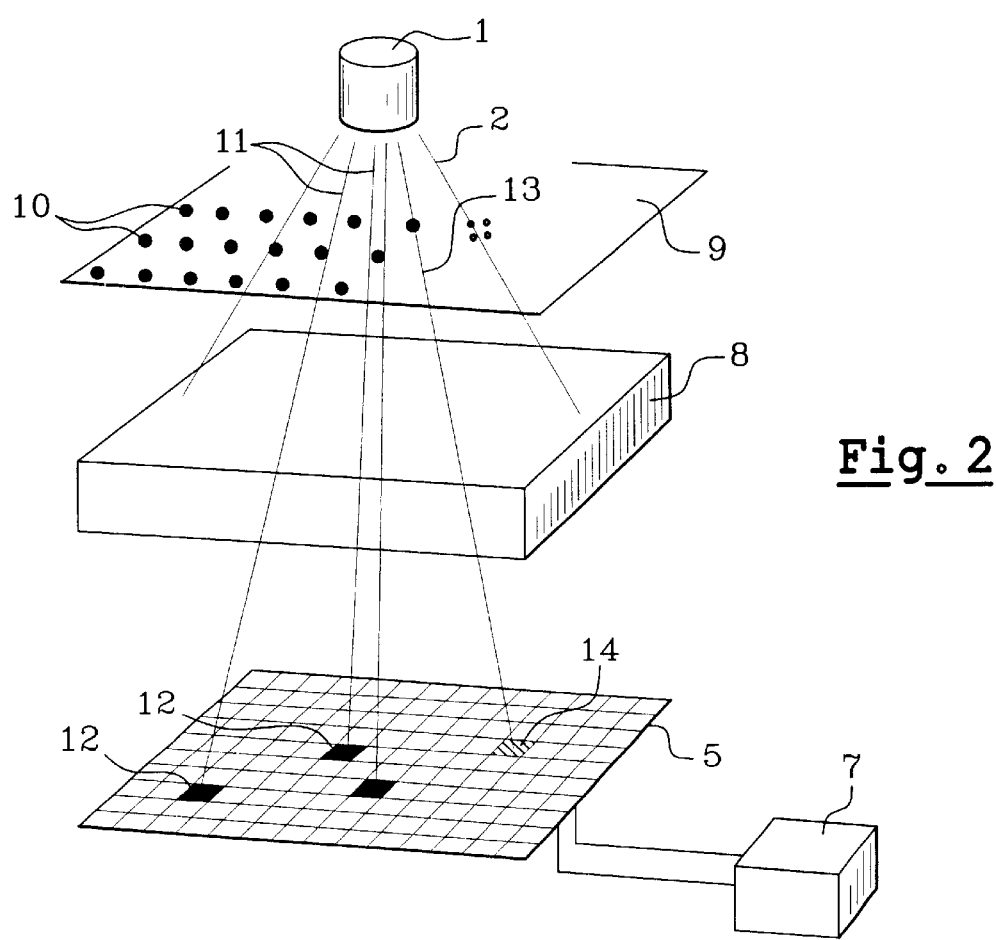
Figure 3:
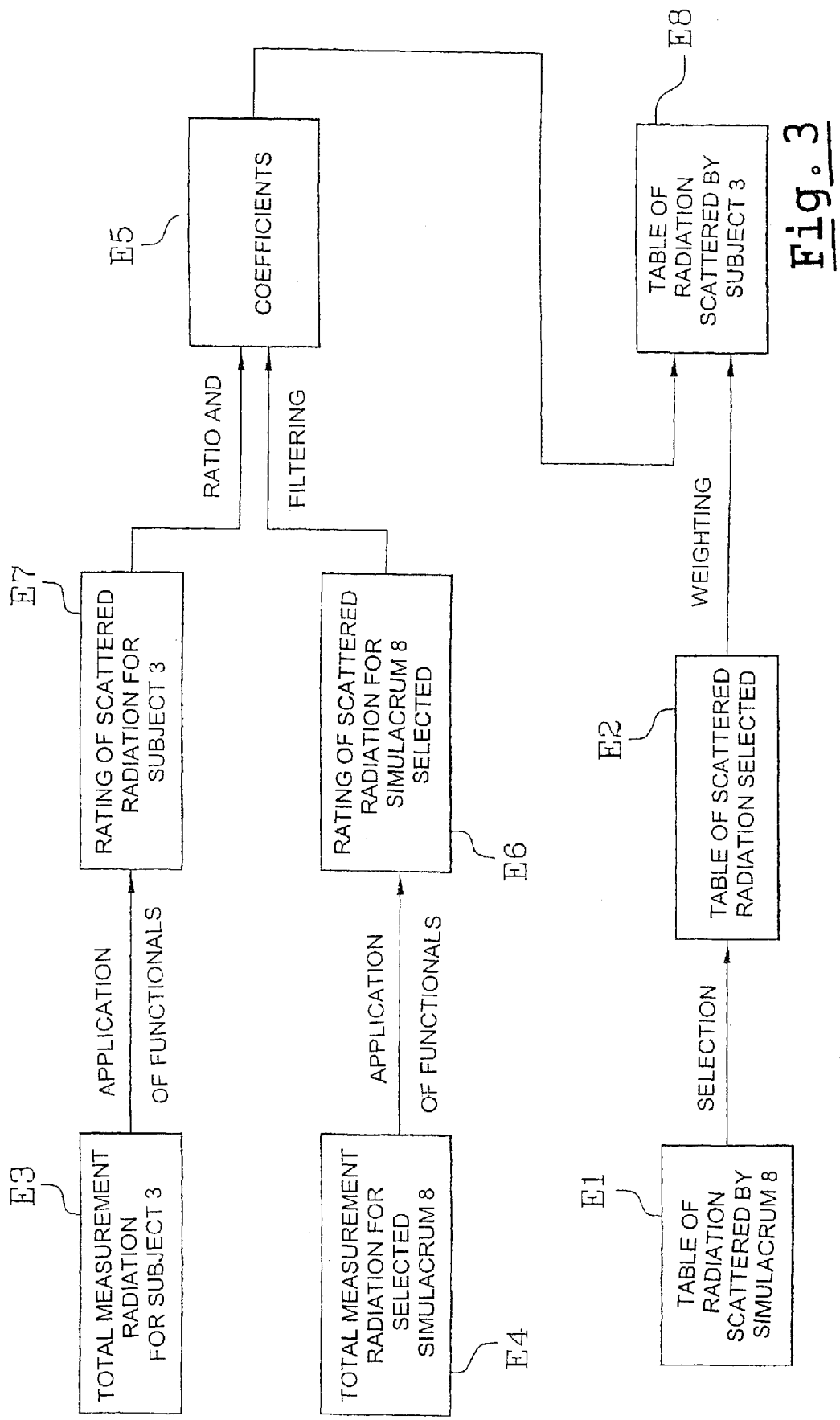

The invention will now be described with reference to the figures, amongst which:

FIG. 1 is a general view of measurement acquisition;
FIG. 2 is a view of calibration acquisition;
FIG. 3 shows the stages of the method.

First of all, reference is made to FIG. 1, where a tube 1 of X-rays emits a conical beam 2 towards a subject to be examined (here, a patient lying on a table 4) then, through the subject, towards a plane network 5 of detectors 6 set in an array. The detectors 6 are connected to an acquisition apparatus 7 and measure scattered radiation which is superposed on the primary radiation, the only one suitable for radiography.

The estimation of scattered radiation through the patient 3 consists first of all of obtaining two-dimensional tables or maps for scattered radiation obtained in comparable circumstances. For this, one carries out standardisation irradiations through simulacra 8 of the subject 30 to be examined, according to FIG. 2: the radiation conditions remain the same, that is one continues to use the tube 1, the beam 2, the network 5 of detectors 6 and the acquisition apparatus 7, the simulacrum 8 replacing the patient; a grid 9 of lead balls 10 is added above the simulacrum 8 and the network 5. The result of this arrangement is that the rays 11 passing through the balls 10 are completely absorbed and the regions 12 of the network 5 located in the prolongation of these rays 11 have detectors 6 which only measure the scattered radiation at these places. It suffices to take these measured values and to interpolate between the regions 12 to make a satisfactory estimation of the scattered radiation issuing from the simulacrum 8 for all the detectors 6 of the network 5.

The simulacrum 8 should be similar to the subject so that the scattered radiation from it is identical. Perfect similarity is not feasible, and this is why one has to use a simulacrum 8 resembling the subject 3 and whose map associated with scattered radiation will be corrected later to evaluate that of the subject. In practice, the simulacrum 8 can be a block of a homogeneous material which possesses the same attenuation coefficient as the base material of the subject 3: in the case of a human body, composed mainly of soft tissue, it is known that Plexiglas (polymethacrylate) is suitable.

In order to allow varied measurements, in reality one has several maps of scattered radiation, obtained for the same number of simulacra 8, which only differ by their thickness and thus by the length of the path crossed by the rays 11. These maps are recorded in a database before real measurements on the subjects 3 to be radiographed. In order to make a map of scattered radiation comparable to that of a subject 3, in practice one selects one of the maps from the database or, better still, a map which has been obtained by interpolation calculations between two of these maps. The selection criterion could be defined by means of a particular ray 13 arriving in a region 14 of the network 5 and which does not pass either through the absorbers 10 of FIG. 2, or through the bone tissues of the patient (or more generally the portions of the subject 3 whose absorption properties are different from the material of the simulacrum 8) in FIG. 1. The total radiation, primary and scattered, received by the region 14 after having crossed each simulacrum 8 will act as index for the corresponding scattered radiation table, and the table selected will have the index for a value identical to the total radiation measured in the region 14 through the subject 3. All of this corresponds to the passage from stage E1 to stage E2 in the flow chart of FIG. 3, which will be explained.

The continuation of the method consists essentially of correcting the table of scattered radiation thus selected in order to adjust it as far as possible to the map of radiation really scattered by the subject 3. In order to carry this out, all available information is used, that is the total radiation received by the detectors 6 beyond the subject 3 and the selected simulacrum 8. This total radiation is called $\Phi t$, the scattered radiation $\Phi d$, the initial radiation issued from the tube 1 $\Phi o$ and the primary radiation $\Phi$, the relation $\Phi t = \Phi + \Phi d$ being respected.

We are now at stages E3 and E4 of the flow chart in FIG. 3. Next, one transforms the values of total radiation $\Phi t$ measured for the subject 3 and the simulacrum 8 selected by applying the functionals to them. More precisely, it is known in prior art that $\Phi d$ is proportional at the first order to $\Phi \log(\Phi/\Phi o)$; this relation, which is deduced from the Klein and Nishina law, gives a general rating of scattered radiation, instead of its intensity.

The initial radiation $\Phi o$ is known; the primary radiation $\Phi$ is not, but it is agreed that this relation should be applied approximately by replacing it by the total radiation $\Phi t$, that is to say that the functional used associates, to each value of total radiation $\Phi t$ measured, the calculated value $\Phi t \log(\Phi t/\Phi o)$, assumed to be close to the scattered radiation $\Phi d$ at this place; one has now reached stages E5 and E6 of the flow chart.

The following stage consists of making, for each of the detectors 6, the relation between the values provided by the functional for the subject 3 and the simulacrum 8 selected according to the formula $$K = \frac{\Phi t \log(\Phi t / \Phi o) \text{subject}}{\Phi t \log(\Phi t / \Phi o) \text{simulacrum}}.$$

The weighting coefficients K thus obtained will serve to deform the map of scattered radiation selected at stage E2 in order to estimate that of the subject 3. The results constitute another two-dimensional table or an array with dimensions identical to that of the radiation tables since it is associated to the network 5 of detectors 6. It is thus possible and advantageous to carry out a spatial digital filtering of this array by applying a lowpass filter which corrects the K coefficients and only conserves the lowest frequencies of their variation and thus probably renders them more in conformity with reality since the scattered radiation varies fairly gradually from one point to another.

When the table of definitive weighting coefficients, called K', has been obtained (at stage E7), it serves to weight the table of scattered radiation selected before at stage E2, to obtain a table of radiation scattered by the subject 3 (stage E8, which constitutes the estimation required)i the formula applied is $\Phi d$ subject=K'$\Phi d$ simulacrum. These $\phi d$ subject estimated values can then be subtracted from the total radiation $\Phi t$ measured by the detectors 6 to estimate the primary radiation $\Phi$ and to obtain a more precise radiographic image of the subject 3.

This method applies to radiography with simple or multiple irradiation energy; in the second case, it is repeated separately for each of the energies used.

The functional proposed here is not the only one which can be used, and the simpler functional $\Phi d = k\Phi$ (approximated further here as $\Phi d = k\Phi t$), k being a constant, could also provide good results for estimating $\phi d$.

What is claimed is:

1. Method for estimation of scattered radiation coming from an initial radiation having crossed a subject (3) and undergoing attenuation letting pass a total measurement radiation characterised by:

drawing up a table of measurements for scattered radiation, obtained by passing the initial radiation through a simulacrum (8) of the subject, calculating coefficients (K') for transposition between the simulacrum and the subject, according to the initial radiation ($\Phi o$), the total measurement radiation through the object ($\Phi t$ subject) and a total measurement radiation through the simulacrum ($\Phi t$ simulacrum), and weighting the measurements table with the transposition coefficients.

2. Method for estimation of scattered radiation according to claim 1, characterised in that the simulacrum (8) is a block of constant thickness and of a homogeneous material, having an attenuation similar to the base material of the subject.

3. Method for estimation of scattered radiation according to claim 1, characterised in that drawing up the measurements table involves a selection in a series of tables of measurements for scattered radiation, obtained by making the initial radiation pass successively through a respective series of simulacra of the subject, which are blocks with different but constant thicknesses and made of a homogeneous material, with attenuation similar to a base material of the subject.

4. Method for estimation of scattered radiation according to claim 3, characterised in that the selection comprises an interpolation between two of the measurement tables.

5. Method for estimation of scattered radiation according to claim 3, characterised in that the selection is made by comparison of a value for the total measurement radiation through the subject and a value for the total measurement radiation through the simulacra.

6. Method for estimation of scattered radiation according to claim 5, characterised in that the comparison is carried out for identical rays (13) of the initial radiation through the subject and the simulacra, only crossing the base material of the subject.

7. Method for estimation of scattered radiation according to claim 1, characterised in that the weighting coefficients are identical functional ratios calculated for the subject and for the simulacrum.

8. Method for estimation of scattered radiation according to claim 7, characterised in that the functionals are equal to the product of the total measurement radiation by the logarithm of the ratio of the total measurement radiation and the initial radiation.

9. Method for estimation of scattered radiation according to claim 1, characterised in that it comprises a lowpass filtering stage for the transposition coefficients set out in a table able to be superposed on the measurements table.

10. Radiography method comprising a correction stage for radiography measurements by subtraction of scattered radiation estimated according to the method according to any one of the above claims.

* * * * *

UNITED STATES PATENT AND TRADEMARK OFFICE
CERTIFICATE OF CORRECTION

PATENT NO. : 6,594,338 B2
DATED : July 15, 2003
INVENTOR(S) : Michel Darboux et al.

It is certified that error appears in the above-identified patent and that said Letters Patent is hereby corrected as shown below:

Title page,
Item [75], Inventors, please delete "Jean-Marc Dinten, Lyons (FR)", and insert therefor -- Jean-Marc Dinten, Lyon (FR) --.
Item [56], References Cited, U.S. PATENT DOCUMENTS, please delete "5,666,381", and insert therefor -- 5,666,391 --.

Column 3,
Line 67, please delete "required)i", and insert therefor -- required); --.

Signed and Sealed this

Twentieth Day of January, 2004

JON W. DUDAS
*Acting Director of the United States Patent and Trademark Office*